United States Patent [19]

Shiah

[11] 4,173,453

[45] Nov. 6, 1979

[54] TOPICAL HAIR COLORING FORMULATION IN THE FORM OF SUSPENSION, LOTION AND CREAM

[75] Inventor: Chyn-Duog Shiah, Manhasset, N.Y.

[73] Assignee: CDC Research Inc., New York, N.Y.

[21] Appl. No.: 884,964

[22] Filed: Mar. 9, 1978

Related U.S. Application Data

[63] Continuation-in-part of Ser. No. 675,485, Apr. 9, 1976, abandoned.

[51] Int. Cl.$^2$ .............................................. A61K 7/13
[52] U.S. Cl. .......................................... 8/10.1; 8/10; 8/10.2; 8/11; 8/32
[58] Field of Search ..................... 8/10, 10.1, 10.2, 11, 8/32

[56] References Cited

U.S. PATENT DOCUMENTS

| | | | |
|---|---|---|---|
| 2,719,104 | 9/1955 | Westerberg | 8/10 |
| 3,075,821 | 1/1963 | Goldemberg et al. | 8/10 |
| 3,215,605 | 11/1965 | Soloway | 8/10.1 |
| 3,838,966 | 10/1974 | Barchas et al. | 8/10.2 X |
| 3,954,393 | 5/1976 | Lapidus | 8/10.1 |

OTHER PUBLICATIONS

Pharmaceutical Formulas, vol. 2, 10th ed., The Chemist and Druggist, London, England, (1946), pp. 253–260.

*Primary Examiner*—James O. Thomas, Jr.
*Assistant Examiner*—Vera C. Clarke
*Attorney, Agent, or Firm*—Robert E. Burns; Emmanuel J. Lobato; Bruce L. Adams

[57] ABSTRACT

Hair coloring formulations in the form of suspensions, lotions, or creams based upon a combination of water-soluble copper salts, water-soluble iron salts and finely divided sulfur are described. No toxic lead salts are used. Hair coloring formulations which contain copper cystine or zinc cystine and finely divided sulfur are also described. These formulations are particularly useful for the gradual coloring of gray hair.

19 Claims, No Drawings

TOPICAL HAIR COLORING FORMULATION IN THE FORM OF SUSPENSION, LOTION AND CREAM

This is a continuation-in-part of my application, Ser. No. 675,485, filed Apr. 9, 1976; now abandoned.

FIELD OF THE INVENTION

The present invention relates to topical hair coloring compositions more particularly to such compositions based on nontoxic metal salts.

BACKGROUND OF THE INVENTION

The dyeing of graying hair is best done when the hair is just starting to turn gray so that the change of appearance does not become striking. The process of hair dyeing is rather messy especially for persons with dark hair. Most hair dyes are aniline-type compounds and the incidences of skin sensitization are the highest among such cosmetic preparations. More recently there are indications that some aniline type dyes may not be safe for general use.

There are several products on the market which have been described as effective for gradually coloring hair to a desired hue. These preparations are based upon the use of heavy metal salts, such as lead salts, in combination with sulfur, a sulfur precursor or a reducing agent. The coloring of hair by such products has two distinct advantages over hair dyes. Because of the slow darkening of the hair, the change of the appearance of a person is not noticeable. Secondly, unlike hair dye, such a preparation colors the growing hair from the root up and during use, the lower section of the hair does not appear white Hair grows approximately 1-3 mm. in 24 hrs. The clear demarkation of the dyed section and the growing section of the hair are often so striking that people must dye their hair again in a few days or weeks. For these reasons the gradual type of hair coloring preparations are popular.

Unfortunately however, the gradual-coloring hair preparations on the market today contain high percentages of lead salts, particularly lead acetate.

Lead is known to be poisonous and can cause mental retardation and even death. It has also been reported in the literature that soluble lead salt can penetrate through the skin. Yet such preparations are allowed to be marketed because of the high demand for their gradual coloring qualities.

SUMMARY OF THE INVENTION

An object of the present invention is to provide new, nontoxic hair coloring compositions by means of which gray hair can be gradually colored to a desired hue.

A further object of the present invention is to provide new, nontoxic hair coloring compositions which are useful in particular for coloring gray hair and which have a beneficial effect on the health of the hair.

A still further object of the present invention is the provision of a new, nontoxic hair coloring composition which is capable of being applied easily by an inexperienced person and which is capable of gradually coloring gray hair.

It has been found now, that a highly effective hair coloring composition which comprises finely divided sulfur and a combination of one or more water-soluble copper salts and one or more water-soluble iron salts either in the form of a suspension, a lotion, or a cream affords gradual coloring of human hair.

It has also been discovered that hair color compositions containing a cystine salt preferably selected from copper cystine and zinc cystine in combination with colloidal elementary sulfur are particularly advantageous.

DESCRIPTION OF THE INVENTION

Typical hair coloring formulations of this invention may be in the form of a suspension, i.e., those formulations which include a relatively large aqueous phase including a relatively small water-soluble surfactant-emollient and an insoluble solid phase. They present compositions which are applied topically to the hair and may be applied daily until the hair is the color desired, after which, for maintenance of the desired color, less frequent application is necessary.

In accordance with one embodiment of the invention, the principal ingredient of the present hair coloring compositions is a salt of copper or zinc. Salts such as the acetate, nitrate or chlorides can be used, however the cystine salt is particularly preferred. Copper and zinc cystine may be used alone or in combination with other copper and zinc salts in the hair coloring compositions of the invention.

Cystine is a water soluble amino acid which is a natural constituent of hair. Naturally occurring proteins such as keratin are thought to be beneficial to hair and skin. Since keratin is a protein obtained from hair, putting it back into hair might be desirable. However, keratins are insoluble in water, as well as aqueous solution of salts, hydrotropic substances, dilute acids and alkalis at room temperature and are also resistant to proteolytic enzymes and resistant to hydrolysis. Therefore it is doubtful whether keratins are absorbed to an appreciable extent by hair follicles. On the other hand keratin is characterized by a high cystine content, and thus cystine, which is water soluble and thus more readily absorbed and/or adsorbed by hair follicles is believed to have a beneficial effect on hair.

A copper compound of cystine is a principal coloring ingredient of a preferred preparation of the invention for turning gray hair to a darker shade. The preparation also contains elemental sulfur. When the copper cystine containing hair coloring preparation of the invention, which is preferably in lotion or cream form, is applied to hair, copper cystine and some sulfur is absorbed and/or adsorbed by the hair follicles or papilla and the following overall reaction occurs:

copper cystine + S → cystine + copper sulfide.

The copper sulfide generated within the hair follicles provides a more or less permanent coloration.

More particularly, in the hair, free sulfur is slowly changed to hydrogen sulfide by the action of microorganisms in the scalp, and the resultant hydrogen sulfide reacts as it is formed with copper cystine to form copper sulfide. Copper sulfide does not attack the skin or scalp as do some coloring agents, such as the black pyrogallol-iron complex. Not only is it undesirable from an appearance point of view to have black dye on the scalp, but such dyes can be absorbed by the skin which may be dangerous.

A further advantage of the copper containing hair coloring compositions of the invention is that copper ion kills or reduces the fungus and yeast in hair and on the scalp which are responsible for the formation of dandruff.

For light hair colors, zinc cystine is a preferred colorant in the hair coloring compositions of the invention. When a composition of the invention containing zinc cystine and sulfur is applied to hair, zinc sulfide which is white to yellowish in color is formed on the hair follicles or papilla in a manner analogous to that of copper sulfide described above. Recent studies by Richard Follis of John Hopkins University have indicated that zinc deficiency affects the growth of hair and therefore it is believed that zinc ion in the compositions of the invention should be beneficial to the well being of human hair.

Copper or zinc cystine may be present in the hair coloring compositions of the invention in an amount of about 0.1 to about 8% by weight, together with about 0.5 to 20% of sulfur, preferably in colloidal form. Iron salts such as ferric chloride, acetate and nitrate, as well as other copper salts such as copper acetate, nitrate and chloride can be used in place of part of the copper cystine; however the preferred compositions of the invention contain at least about 0.1 to 1% of copper or zinc cystine. Likewise part of the zinc cystine, in formulations for light hair can be replaced with other non-toxic zinc salts, such as zinc chloride and nitrate.

In another embodiment of the invention, the hair coloring preparation in suspension form contains from 0.2 to about 3% of copper salts, such as copper acetate, nitrate or chloride; from 0.1 to about 3% of iron salts, such as ferric chloride, acetate or nitrate; and from 0.5 to about 20% of sulfur in finely divided form preferably colloidal sulfur.

With regard to the lotion and cream formulation of this invention, the lotions and creams include a relatively large aqueous phase and a relatively small oil phase which may contain one or more emollients, emulsifiers and thickeners. Other solids or colloids may be included in either phase or may comprise an interphase.

The following examples further illustrate the best modes currently contemplated for carrying out the present invention, but the examples must not be construed as limiting the invention in any manner. All temperatures are expressed in degrees Centigrade.

EXAMPLE 1

Suspension

| | |
|---|---|
| Sulfur, colloidal | 1.0 gm. |
| Cupric acetate, $Cu(C_2H_3O_2)_2 \cdot H_2O$ | 0.5 gm. |
| Ferric chloride, $FeCl_3$ | 0.2 gm. |
| Propylene glycol | 5.0 gm. |
| "BRIJ35", Polyoxyethylene fatty alcohol ether (ICI) | 3.0 gm. |
| Alcohol, U.S.P. | 20.0 cc. |
| Perfume | 0.05 cc. |
| Purified water, sufficient to make | 100.0 cc. |

Dissolve perfume and BRIJ35 in alcohol. Add gradually with continuous mixing about 20 cc. of purified water to obtain a clear solution.

Dilute the solution with about 50 cc. of water. Add cupric acetate, ferric chloride, propylene glycol and mix to dissolve. Incorporate colloidal sulfur into the solution, add sufficient purified water to make 100 cc. and agitate for 5 minutes. The filling of the suspension into bottles should be done during agitation in order to fill a homogenous suspension of the components into the bottle.

The product when applied to live hair gradually imparts a black or brunette coloration comparable to that attained by commercial lead-containing preparations.

EXAMPLE 2

Suspension

| | |
|---|---|
| Sulfur, colloidal | 1.0 gm. |
| Copper cystine $Cu[O_2C-CH(NH_2)CH_2-S-]_2$ | 0.7 gm. |
| Ferric chloride, $FeCl_3$ | 0.2 gm. |
| Propylene glycol | 5.0 gm. |
| "BRIJ35", Polyoxyethylene fatty alcohol ether (ICI) | 3.0 gm. |
| Alcohol, U.S.P. | 20.0 cc. |
| Perfume | 0.05 cc. |
| Purified water, sufficient to make | 100.0 cc. |

Dissolve perfume and BRIJ35 in alcohol. Add gradually with continuous mixing about 20 cc. of purified water to obtain a clear solution.

Dilute the solution with about 50 cc. of water. Add copper cystine, ferric chloride, propylene glycol and mix to dissolve. Incorporate colloidal sulfur into the solution, add sufficient purified water to make 100 cc. and agitate for 5 minutes. The filling of the suspension into bottles should be done during agitation in order to fill a homogeneous suspension of the components into the bottle.

The product gradually imparts black or brunette coloration when applied to live hair.

EXAMPLE 3

Lotion

| | |
|---|---|
| Sulfur, colloidal | 1.0 gm. |
| Cupric acetate, $Cu(C_2H_3O_2)_2 \cdot H_2O$ | 0.5 gm. |
| Ferric Chloride, $FeCl_3$ | 0.2 gm. |
| Propylene glycol | 5.0 gm. |
| BRIJ35, (Polyoxyethylene fatty alcohol ether), ICI | 3.0 gm. |
| Cetyl alcohol | 1.0 gm. |
| Stearyl alcohol | 2.0 gm. |
| Methylparaben | 0.15 gm. |
| Propylparaben | 0.02 gm. |
| Alcohol | 1.0 cc. |
| Perfume about | 0.05 cc. |
| Purified water, sufficient to make | 100.0 cc. |

Dissolve cupric acetate and ferric chloride in 80 cc. of purified water, add propylene glycol and heat to 80°–85° C. Melt cetyl alcohol, stearyl alcohol, and BRIJ35 together and heat to 80°–85° C. Add the sulphur. Add the hot aqueous solution, at first slowly with vigorous agitation to emulsify and then once the emulsion has started, the remainder of the solution may be added more rapidly into the batch. Mix and then cool down to 50° C. with continuous rapid agitation. Continue the cooling rate with slower agitation to allow the emulsion to congeal. Dissolve the parabens and the perfume in alcohol and incorporate into the batch. Add additional water, with mixing, at about 48°–50° C. into the emulsion. Continue to mix at a slow rate until the temperature reaches 42° C. Stop agitation. Allow to cool to room temperature. Bottle at room temperature.

The product when applied to live hair gradually imparts a black or brunette coloration comparable to that attained by commercial lead-containing preparations.

EXAMPLE 4

Lotion

| | |
|---|---|
| Sulfur, colloidal | 1.0 gm. |
| Copper cystine, $Cu[O_2C\text{-}CH(NH_2)CH_2\text{-}S\text{-}]_2$ | 1.2 gm. |
| Propylene glycol | 5.0 gm. |
| BRIJ35, (Polyoxyethylene fatty alcohol ether), ICI | 3.0 gm. |
| Cetyl alcohol | 1.0 gm. |
| Stearyl alcohol | 2.0 gm. |
| Methylparaben | 0.15 gm. |
| Propylparaben | 0.02 gm. |
| Alcohol | 1.0 cc. |
| Perfume about | 0.05 cc. |
| Purified water, sufficient to make | 100.0 cc. |

Dissolve copper cystine in 80 cc. of purified water, add propylene glycol and heat to 80°–80° C. Melt cetyl alcohol, stearyl alcohol, and BRIJ35 together and heat to 80°–85° C. Add the sulfur. Add the hot aqueous solution, at first slowly with vigorous agitation to emulsify and then once the emulsion has started, the remainder of the solution may be added more rapidly into the batch. Mix and then cool down to 50° C. with continuous rapid agitation. Continue the cooling rate with slower agitation to allow the emulsion to congeal. Dissolve the parabens and the perfume in alcohol and incorporated into the batch. Add additional water, with mixing, at about 48°–50° C. into the emulsion. Continue to mix at a slow rate until the temperature reaches 42° C. Stop agitation. Allow to cool to room temperature. Bottle at room temperature.

The product when applied to live hair gradually imparts a black or brunette coloration comparable to that attained by commercial lead-containing preparations.

EXAMPLE 5

Lotion

| | |
|---|---|
| Sulfur, colloidal | 1.0 gm. |
| Cupric acetate, $Cu(C_2H_3O_2)_2 \cdot H_2O$ | 0.5 gm. |
| Ferric chloride, $FeCl_3$ | 0.2 gm. |
| Propylene glycol | 5.0 gm. |
| Polawax, (croda co.) | 2.0 gm. |
| Mineral Oil, heavy, U.S.P. | 5.0 gm. |
| Alcohol, U.S.P. | 0.15 gm. |
| Methylparaben, U.S.P. | 0.02 gm. |
| Propylparaben, U.S.P. | 0.02 gm. |
| Perfume about | 0.05 cc. |
| Purified water, sufficient to make | 100.0 cc. |

Dissolve cupric acetate and ferric chloride in about 80 cc. of water, mix in propylene glycol, and heat to 80° C.–85° C. Melt Polawax and mineral oil together and heat to 80°–85° C. Mix the aqueous phase with the oil phase with vigorous agitation to emulsify. Cool the emulsion to 50° C. and continue to mix at a slow rate. Dissolve the parabens and the perfume in alcohol and mix into the batch. Add colloidal sulfur and sufficient purified water to make 100 cc. and continue mixing until congealed to a lotion. Stop mixing when the temperature reaches 40° C. Bottle while warm.

The product when applied to live hair gradually imparts a black or brunette coloration comparable to that attained by commercial lead-containing preparations.

EXAMPLE 6

Lotion

| | |
|---|---|
| Sulfur, colloidal | 1.0 gm. |
| Cupric acetate, $Cu(C_2H_3O_2)_2 \cdot H_2O$ | 0.5 gm. |
| Copper cystine $Cu[O_2CCH(NH_2)CH_2\text{-}]_2$ | 0.4 gm. |
| Propylene glycol | 5.0 gm. |
| Polawax, (croda co.) | 2.0 gm. |
| Mineral Oil, heavy U.S.P. | 5.0 cc. |
| Alcohol, U.S.P. | 1.0 cc. |
| Methylparaben, U.S.P. | 0.15 gm. |
| Propylparaben, U.S.P. | 0.02 gm. |
| Perfume about | 0.05 cc. |
| Purified water, sufficient to make | 100.0 cc. |

Dissolve copper acetate and copper cystine in about 80 cc. of water, mix in propylene glycol, and heat to 80° C.–85° C. Melt Polawax and mineral oil together and heat to 80°–80° C. Mix the aqueous phase with the oil phase with vigorous agitation to emulsify. Cool the emulsion to 50° C. and continue to mix at a slow rate. Dissolve the parabens and the perfume in alcohol and mix into the batch. Add colloidal sulfur and sufficient purified water to make 100 cc. and continue mixing until congealed to a lotion. Stop mixing when the temperature reaches 40° C. Bottle while warm.

The product gradually imparts a black or brunette coloration when applied to live hair.

EXAMPLE 7

Cream

| | |
|---|---|
| Sulfur, colloidal | 1.0 gm. |
| Cupric acetate, $Cu(C_2H_3O_2)_2 \cdot H_2O$ | 0.5 gm. |
| Ferric chloride, $FeCl_3$ | 0.2 gm. |
| Propylene glycol | 5.0 gm. |
| BRIJ78, (Polyoxyethylene fatty alcohol ether) | 3.0 gm. |
| Cetyl alcohol | 1.5 gm. |
| Stearyl alcohol | 3.5 gm. |
| Alcohol, U.S.P. | 1.0 cc. |
| Methyl paraben, U.S.P. | 0.15 gm. |
| Propylparaben, U.S.P. | 0.02 gm. |
| Petrolatum, U.S.P. | 18.0 gm. |
| Perfume about | 0.05 cc. |
| Purified water sufficient to make | 100.0 cc. |

Dissolve cupric acetate and ferric chloride in about 60 cc. or purified water, add propylene glycol, mix, and heat to 80°–85° C. Melt together BRIJ78, cetyl alcohol, stearyl alcohol and petrolatum, mix, and heat to 80° C.–85° C. Add the oil phase with vigorous agitation into the aqueous phase to emulsify. Cool the emulsion to 50° C. and continue to mix at a slow rate. Dissolve the parabens and the perfume in alcohol and mix into the batch. All colloidal sulfur and sufficient water to make 100 cc. and continue slow rate of agitation until the cream congeals at 42° C. and stop agitation. Bottle while warm.

The product when applied to live hair gradually imparts a black or brunette coloration comparable to that attained by commercial lead-containing preparations.

EXAMPLE 8

Cream

| | | |
|---|---|---|
| Sulfur, colloidal | | 1.0 gm. |
| Cupric acetate, $Cu(C_2H_3O_2)_2 \cdot H_2O$ | | 0.5 gm. |
| Ferric chloride, $FeCl_3$ | | 0.2 gm. |
| Propylene glycol | | 5.0 gm. |
| Polawax, (Croda Co.) | | 8.0 gm. |
| Petrolatum, U.S.P. | | 17.0 gm. |
| Alcohol, U.S.P. | | 1.0 gm. |
| Methylparabens, U.S.P. | | 0.15 gm. |
| Propylparaben, U.S.P. | | 0.02 gm. |
| Perfume | about | 0.05 cc. |
| Purified water, sufficient to make | | 100.0 cc. |

Dissolve cupric acetate and ferric chloride in about 60 cc. of purified water, add propylene glycol, mix, and heat to 80°-85° C. Melt together Polawax and petrolatum, mix and heat to 80°-85° C. Add the oil phase into the aqueous phase with vigorous agitation to emulsify. Cool the emulsion to 50° C. and continue to mix at a slow rate. Dissolve parabens and the perfume in alcohol and mix into the batch. Add colloidal sulfur and sufficient water to 100 cc. and continue to mix at a slow rate until the cream congeals at about 42° C. and stop agitation. Bottle when warm.

The product when applied to live hair gradually imparts a black or brunette coloration comparable to that attained by commercial lead-containing preparations.

EXAMPLE 9

Cream

| | | |
|---|---|---|
| Sulfur, colloidal | | 1.0 gm. |
| Zinc cystine $Zn[O_2CCH(NH_2)CH_2S-]_2$ | | 1.2 gm. |
| Propylene glycol | | 5.0 gm. |
| Polawax, (Croda Co.) | | 8.0 gm. |
| Petrolatum, U.S.P. | | 17.0 gm. |
| Alcohol, U.S.P. | | 1.0 gm. |
| Methylparabens, U.S.P. | | 0.15 gm. |
| Propylparaben, U.S.P. | | 0.02 gm. |
| Perfume | about | 0.05 cc. |
| Purified water, sufficient to make | | 100.0 cc. |

Dissolve zinc cystine in about 60 cc. of purified water, add propylene glycol, mix, and heat to 80°-85° C. Melt together BRIJ78, cetyl alcohol, stearyl alcohol and petrolatum, mix, and heat to 80° C.-85° C. Add the oil phase with vigorous agitation into the aqueous phase to emulsify. Cool the emulsion to 50° C. and continue to mix at a slow rate. Dissolve the parabens and the perfume in alcohol and mix into the batch. Add colloidal sulfur and sufficient water to make 100 cc. and continue slow rate of agitation untl the cream congeals at 42° C. and stop agitation. Bottle while warm.

The product gradually imparts a white to yellow coloration when applied to live hair.

As can be seen from the above examples, any pharmaceutically acceptable vehicle may be used if it is suitable for topical application to the hair. By pharmaceutically acceptable it is understood that the vehicle ingredients do not cause incompatibilities with the active components, i.e., the copper or zinc salts, the iron salts and/or the sulfur.

Generally all topically acceptable copper or zinc salts, soluble to the extent of at least 0.1% in water, are suitable. Among suitable copper salts in addition to copper cystine are copper acetate, copper sulfate, copper chloride, copper bromide, copper ammonium chloride, copper ammonium citrate and copper citrates. Suitable zinc salts in addition to zinc cystine include the acetate and chloride. Either cupric or cuprous salts may be used if topically acceptable. The copper or zinc salt should be present in the composition to the extent of arom 0.1 to about 8% with the preferred range being between about 0.2 and 1.5 wt. %.

Generally, all topically acceptable iron salts, water soluble at least to the extent of 0.05% may be used. Among suitable iron salts for the composition of this invention are iron sulfate, iron chloride, iron bromide, iron citrate, iron tartrate, ferric sodium citrate, ferric potassium citrate, ferric glycerophosphate, ferric ammonium sulfate. The iron salt should be present in the composition to the extent of from 0.05 to 3% with 0.1 to 1% being preferred. Either the ferric or ferrous form of iron may be used if topically acceptable.

The sulfur for use in the composition of this invention, must be in finely divided form and generally of a pharmaceutically acceptable grade as set forth in the Merck Index. The particular size should be less than 100 microns in any major dimension. The various pharmaceutical grades of precipitated or colloidal sulfur; or ground, washed sulfur; or sublimed sulfur of proper size as indicated above may be used. The sulfur should be present in the composition to the extent of from 0.1 to 20% with the preferred range being between 0.5 to 10%.

The vehicle for topical application may comprise appropriate oils, wetting agents, emulsifiers, perfumes, hair conditioners and other compatible ingredients in addition to water.

Suspensions include aqueous solutions of the iron and copper salts with the insoluble sulfur dispersed therein. Creams, lotions and gels are usually colloidal emulsions or thickened solutions containing gums, surfactants, lipids, oils and emulsifiers as are common for such vehicles, and have the active ingredients dissolved and/or suspended therein.

Heavy metals such as lead, silver and bismuth salts are to be avoided. While such salts cause hair coloration, they are toxic when used internally and constant exposure during application and contact of the hair, treated with such toxic materials, provides an avoidable hazard even if they are minimally absorbed through the skin. The present invention not only provides a method and composition for avoiding this hazard, but a method and composition which is beneficial for the hair while gradually adding color thereto.

The above examples are merely illustrative of the scope of this invention. Except for the zinc salts, copper salts, iron salts and sulfur, all other ingredients may be substituted by their artrecognized equivalents. All parts and percentages recited herein unless otherwise specified are parts and percentages by weight.

What I claim and desire to protect by Letters Patent is:

1. A composition for coloring gray hair for topical application which comprises as active coloring agent, a salt selected from the group consisting of copper cystine or zinc cystine in an amount of about 0.1 to 8% by weight of said composition in admixture with sulfur in finely divided form in an amount of about 0.5 to 20% of said composition in an aqueous pharmaceutically acceptable vehicle for topical application.

2. A composition according to claim 1, which contains zinc cystine.

3. A composition according to claim 1, which contains zinc cystine and furthr comprises another nontoxic water soluble zinc salt.

4. A composition according to claim 1, which contains copper cystine.

5. A composition according to claim 1, which contains copper cystine and further comprises at least one salt selected from the group consisting of a water soluble nontoxic iron salt and another water soluble nontoxic copper salt.

6. A composition in accordance with claim 1, in which said salt is present in an amount of about 0.1 to 1% by weight.

7. A composition of claim 5, wherein said copper salt is selected from the group consisting of copper acetate, copper sulfate, copper chloride, copper bromide, copper ammonium chloride, copper ammonium citrate, and copper citrate.

8. A composition of claim 5, wherein said iron salt is selected from the group consisting of iron sulfate, iron chloride, iron bromide, iron citrate, iron tartrate, ferric sodium citrate, ferric potassium citrate, ferric glycerophosphate, ferric ammonium citrate, ferric ammonium tartrate, and ferric ammonium sulfate.

9. A composition of claim 1, wherein said finely divided sulfur has a particle size with a major dimension of less than 100 microns.

10. A composition of claim 1, wherein said sulfur is a pharmaceutical sulfur selected from the group consisting of precipitated sulfur, sublimed sulfur, colloidal sulfur and washed sulfur.

11. A composition of claim 1 wherein said vehicle is selected from the group consisting of a suspension, a lotion, a gel and a cream.

12. A composition for coloring gray hair which consists of a topical application comprising a combination of at least one water-soluble copper salt in an amount of about 0.1 to 8% by weight, at least one water-soluble iron salt in an amount of about 0.05 to 3% by weight and a finely divided form of sulfur in an amount of about 0.1 to 20% by weight in an aqueous, pharmaceutically acceptable vehicle for topical application.

13. A composition as defined in claim 12 which contains about 0.2 to 3% by weight of said copper salt, about 0.1 to 3% by weight of said iron salt and about 0.5 to 20% by weight of said sulfur.

14. A composition according to claim 12, which contains copper cystine as the principal copper salt.

15. A composition of claim 12, wherein said iron and copper salts are each present in the range from 0.5 to 3% by weight.

16. A composition of claim 12, wherein said copper salt is present in the range of about 0.2 to 1%; said iron salt is present in the range of about 0.1 to 1%; and said sulfur is present in the range of about 0.5 to 10%.

17. A method of coloring gray hair to white and blonde shades which comprises topically applying the composition of claim 2 to said hair periodically in an amount effective to color said hair.

18. A method of coloring gray hair to black and brunette shades which comprises topically applying the composition of claim 4 to said gray hair periodically in an amount effective to color said hair.

19. A method of coloring gray hair to black and brunette shades which comprises topically applying of the composition of claim 12 to said gray hair periodically in an amount effective to color said hair.

* * * * *